United States Patent
Teder

[19]

[11] Patent Number: 5,898,183
[45] Date of Patent: Apr. 27, 1999

[54] COMPACT MOISTURE SENSOR WITH EFFICIENT HIGH OBLIQUITY OPTICS

[75] Inventor: Rein S. Teder, Bloomington, Minn.

[73] Assignee: Libbey-Owens-Ford Co., Toledo, Ohio

[21] Appl. No.: 08/951,922

[22] Filed: Oct. 16, 1997

[51] Int. Cl.⁶ .................................................. H01J 5/16
[52] U.S. Cl. ................. 250/574; 250/227.25; 250/341.8; 318/483; 340/602
[58] Field of Search ............................... 250/574, 227.25, 250/239, 341.8; 318/483, DIG. 2; 340/602

[56] References Cited

U.S. PATENT DOCUMENTS

| | | |
|---|---|---|
| 4,355,271 | 10/1982 | Noack . |
| 4,620,141 | 10/1986 | McCumber et al. . |
| 4,652,745 | 3/1987 | Zabardelli . |
| 4,676,638 | 6/1987 | Yasuda . |
| 4,701,613 | 10/1987 | Watanabe et al. . |
| 4,798,956 | 1/1989 | Hochstein . |
| 4,859,867 | 8/1989 | Larson et al. . |
| 4,871,917 | 10/1989 | O'Farrell et al. . |
| 4,930,742 | 6/1990 | Schofield et al. . |
| 4,973,844 | 11/1990 | O'Farrell et al. ..................... 250/341.8 |
| 5,015,931 | 5/1991 | Muller . |
| 5,203,207 | 4/1993 | Sugiyama . |
| 5,262,640 | 11/1993 | Purvis et al. . |
| 5,278,425 | 1/1994 | Bendicks . |
| 5,323,637 | 6/1994 | Bendicks et al. . |
| 5,391,891 | 2/1995 | Wiegleb et al. . |
| 5,414,257 | 5/1995 | Stanton . |
| 5,498,866 | 3/1996 | Bendicks et al. . |
| 5,533,391 | 7/1996 | Brade et al. . |
| 5,560,245 | 10/1996 | Zettler et al. . |
| 5,568,027 | 10/1996 | Teder . |
| 5,572,017 | 11/1996 | Veltum et al. . |
| 5,581,240 | 12/1996 | Egger . |
| 5,598,146 | 1/1997 | Schöder . |
| 5,661,303 | 8/1997 | Teder . |

FOREIGN PATENT DOCUMENTS

| | | |
|---|---|---|
| PCT/DE95/ 00144 | 2/1994 | European Pat. Off. . |
| 96104774 | 3/1996 | European Pat. Off. . |

*Primary Examiner*—Stephone Allen
*Attorney, Agent, or Firm*—Marshall & Melhorn

[57] ABSTRACT

A compact moisture sensor for mounting on the inner surface of a windshield to detect moisture, such as rain, on the outer surface of the windshield and control the windshield wipers accordingly includes a coupler having a collimator and focuser and a housing for detachably covering the coupler. A planar circuit board disposed within the housing includes emitters and detectors mounted such that the axes of emission and detection are perpendicular to the windshield when the housing is secured to the coupler. The collimator and focuser are disposed adjacent the emitter and detector respectively such that the optical axes of the collimator and focuser form oblique angles with respect to the emission and detection axes. Two emitters and two detectors are used to form four optical paths of equal length and optical efficiency. In operation, a light beam from the emitter enters the windshield at a forty-five degree angle and is reflected back from the outer surface of the windshield to the detector, which generates a control signal based on the amount of light reflected from the outer surface. Moisture on the outer surface of the windshield reduces the amount of light reflected to the detector which signals control circuitry for operating the windshield wipers.

20 Claims, 5 Drawing Sheets

COMPACT MOISTURE SENSOR WITH EFFICIENT HIGH OBLIQUITY OPTICS

BACKGROUND OF THE INVENTION

The present invention relates generally to an optical moisture sensor for mounting upon the interior surface of a windshield, and more particularly, to a compact optical moisture sensor having optical emitters, detectors, and optical components mounted on a planar circuit board which is positioned parallel to the interior surface. A coupler having collimator and focusing lenses is used to refract light beams as the light beams travel from the emitters, and is reflected from the outer surface of the windshield back to the detectors.

Motor vehicles have long been equipped with motor-driven windshield wipers for clearing moisture from the external surface of the windshield, at least within the driver's field of vision, and generally over a larger area so as to enhance vision through the windshield. In most vehicles today, the windshield wiper system includes multi-position or variable speed switches which allow the driver to select a wide, if not an infinitely variable, range of speeds to suit conditions. Wiper controls are manually operated and typically include a delay feature whereby the wipers operate intermittently at selected time delay intervals.

Wiper control systems have recently been developed which include a moisture sensor mounted on the windshield to automatically activate the motor when moisture is deposited upon the surface of the windshield or other vehicle window upon which a wiper may be employed, such as the rear window. By sensing rain or other moisture on the glass surface, the wipers can be controlled accordingly. Such wiper control systems free the driver from the inconvenience of frequently adjusting the wiper speed as the driving conditions change. Wiper control systems with optical moisture sensors have been incorporated into the production of several models of passenger cars. In order to increase the commercial use and consumer acceptance of the wiper control systems, there is a need for a more compact and less expensive optical moisture sensor.

Wiper control systems have employed a number of different technologies to sense the moisture conditions encountered by a vehicle, including conductive, capacitive, piezoelectric, and optical sensors. Optical sensors operate upon the principle that a light beam is diffused or deflected from its normal path by the presence of moisture on the exterior surface of the windshield. The systems which employ optical sensors have the singular advantage that the means of sensing disturbances in an optical path is directly related to the phenomena observed by the driver (i.e., disturbances in the optical path that affords the driver vision).

Noak (U.S. Pat. No. 4,355,271) discloses an optical moisture sensor having optical components mounted in a box-like housing attached to the interior surface of the windshield. The moisture sensor devices for controlling the windshield wipers of a vehicle as disclosed by McCumber et al. and Teder (U.S. Pat. Nos. 5,059,877 and 5,239,244) also disclose a box-like housing mounted upon the interior surface of the windshield for enclosing the optics and electronics.

In optical moisture sensors, light from an emitter is directed into the windshield at an angle of approximately forty-five degrees with respect to the windshield. The light is then reflected by the outer surface of the windshield at approximately a forty-five degree angle and is directed into a detector. The presence of moisture on the surface of the windshield affects the reflection of light at the air-glass interface at the outer surface of the windshield, and this change in reflected light is electronically processed and utilized as the signal for activating the windshield wipers. McCumber et al. (U.S. Pat. No. 4,620,141) disclose an automatic control circuit for triggering a sweep of the wiper blades in response to the presence of water droplets on the exterior surface of a windshield.

When the angle of entry of the light beam into the windshield is greater than fifty degrees, a loss of signal frequently occurs. When the angle of entry is less than forty degrees, a loss of sensitivity occurs and the sensor is not able to properly detect moisture on the windshield. Consequently, it is essential that the angle of entry of the light beam from the emitter enter the windshield at approximately forty-five degrees.

The desired forty-five degree angle can be achieved by mounting the optoelectronic devices (emitters and detectors) at forty-five degree angles or by deflecting the light as it travels between the devices and the glass windshield. Stanton (U.S. Pat. No. 5,414,257) discloses an optical sensor having optoelectronic devices mounted on a circuit board at an appropriate angle with respect to the surface of the glass such that their optical axis' extend at the appropriate forty-five degree angle or can be deflected so as to do so. Stanton teaches devices cast from flexible epoxy resin and the bending of the leads of the devices at an angle to facilitate the angled mounting. The problem with bending the leads of the electronic devices is that most automated component insertion equipment cannot insert components with bent leads which increases the cost of assembling the circuit boards. In addition, the bent lead devices are less reliable from a performance standpoint.

The mounting of optoelectronic devices on circuit boards without bending the leads is disclosed in Zettler (U.S. Pat. No. 5,560,245). The emitters and detectors are mounted on small satellite circuit boards which are angled with respect to the main circuit board. The satellite circuit boards are angled to aligned the emitters and detectors at the appropriate forty-five degree angle with the windshield. Although this mounting configuration does not require lead forming, the use of such small circuit boards creates other problems. The small circuit boards used to mount the optoelectronic devices cannot accommodate the signal processing circuitry, which must be located on a separate circuit board. The use of multiple circuit boards and the orientation of the circuit boards in the housing of the sensor increases the size and cost of the sensor.

Conventional optoelectronic devices, including the new surface-mount technology devices (SMT's), are generally designed so that the optical axis is perpendicular to the circuit board on which they are mounted. Teder (U.S. Pat. No. 5661,303) discloses the use of a single circuit board mounted co-planar with the surface of the windshield which results in a low cost and compact sensor enclosure. However, this design requires optical components having optical axis which are approximately parallel to the optical axis of the optoelectronic devices. It is desirable to reduce the size and cost of the optical components to further reduce the size and cost of the moisture sensor.

Another way to reduce the size and cost of the optical sensor includes reducing the number of optoelectonic components. Noak discloses using a single detector to simultaneously detect two or more emitters. Muller (U.S. Pat. No. 5,015,931) discloses that several beams may be derived from a single nondirectional emitter. Such configurations provides the desired area of detection with a fewer number of detectors. McCumber et al. (U.S. Pat. No. 4,620,141) teach that a balanced configuration tends to reject the effect of ambient light. Emitters, however, typically vary by about 2:1 in signal strength. This has limited the ability of prior art optical moisture sensor systems to achieve a good signal balance. The optical paths shown by Muller in '931 are of unequal length. Thus, the paths would be of differing optical efficiency and could not be used to make a well-balanced system. Teder (U.S. Pat. No. 5,661,303) uses four emitters and two detectors to achieve four optical paths of equal length, however it is desirable to reduce the size and cost of the moisture sensor by using even fewer components.

The optical moisture sensor should securely engage the windshield and the optics contained therein should be optically coupled to the windshield so as to effectively eliminate the interface between the light emitters-detectors and glass surface from an optical standpoint. Purvis (U.S. Pat. No. 5,262,640) describes an intermediate adhesive interlayer for affixing the sensor housing and the optics contained therein to the windshield. The sensor housing is affixed directly to the surface of the windshield or other vehicle window by means of an intermediate interlayer disposed between the sensor housing and the interior surface of the windshield.

Vehicle manufactures desire a sensor which is already installed at the windshield manufacturer, or a sensor that is very easy to install on the vehicle production line. The windshield manufacturer ships windshields nested together such that there is very little spacing for mounting a sensor.

Schofield (U.S. Pat. No. 4,930,743) discloses the use of a bracket, such as a rear view mirror bracket, for mounting the optical moisture sensor. This approach necessitates additional support structure or the addition of silicone pieces to optically couple the moisture sensor to the windshield. A bracket mounting systems results in additional parts and increased costs.

Bendix (U.S. Pat. No. 5,278,425) and Stanton ('257) teach that a lens may be permanently affixed to the windshield such that a sensor housing may be detachably mounted on the lens. The lens may impart focal power to the beam, as shown in Bendix. Alternatively, the lens may couple the beams to the windshield through planar surfaces normal to the beam direction, as disclosed in Stanton. However, both Bendix and Stanton require a lens that is approximately as thick as the windshield. When stacking the windshields for transportation from the glass manufacturer to the vehicle assembly line, the additional space necessitated for the lens adds additional handling costs to the cost of the windshield. It is desirable to have a sensor which is attached to the windshield and is thin enough not to interfere with nesting the windshields during shipping.

Modern solar-control windshields, such as windshields sold under the trademark "EZ-KOOL" commercially available from Libbey-Owens-Ford Co., absorb the infrared rays used by many optical moisture sensors. Sensors without coupling or light gathering optics are likely to be too inefficient for use on these windshields. In German Patent No. DE 3314770 to Kohler, et. al., lenses in a coupler increase the sensed area and efficiency of a moisture sensor. Watanabe (U.S. Pat. No. 4,701,613) discloses a series of V-grooves that couples rays into and out of a windshield with an improved efficiency, however, the devices are mounted at a forty-five degree angle with respect to the glass surface because the grooves do not gather diverging light rays and focus them onto the detector. It is desirable to mount the optoelectronic components on a single planar circuit board while improving the efficiency of the optical moisture sensor for use on modern solar-control windshields.

SUMMARY OF THE INVENTION

The present invention relates to a moisture sensor for mounting on a first surface of a sheet of glass to detect moisture in a sensing area on a second surface of the sheet of glass. The moisture sensor includes a coupler to be mounted on the first surface of the sheet of glass for coupling light rays into and out of the glass and a housing detachably secured to the coupler. A planar circuit board is secured in the housing and has a device surface which is disposed generally parallel to the first surface of the sheet of glass. An emitter for emitting light rays about an emission axis is mounted on the device surface. The emission axis extends from the emitter approximately perpendicular to the device surface of the circuit board. A collimator for collimating light rays from the emitter into a collimated light beam has an aperture with a physical center and an optical center spaced apart from the physical center. An optical axis extends through the optical center. The emitter and the collimator are disposed such that the optical axis forms a first oblique angle with respect to the emission axis.

A detector having a detection surface and a detection axis extending from the detection surface is mounted on the device surface of the planar circuit board such that the detection axis is approximately perpendicular to the device surface. The detector detects light striking the detection surface and generates signals in response to the detected light. The coupler also includes a focuser for focusing the collimated light beam onto the detection surface. The focuser has an aperture with a physical center and an optical center spaced apart from the physical center. An optical axis extends through the optical center. The focuser and the detector are disposed such that the optical axis forms a second oblique angle with respect to the detection axis.

The sensor is provided with multiple emitter-detector optical systems to provide an array of sensed areas. A pair of emitters is used in conjunction with a pair of detectors to achieve four separate optical paths of equal length and four sensing areas on the glass surface. The emitters and detectors form a balanced electrical system which is electrically connected to the windshield wiper control circuitry to control operation of the wiper system.

An efficient and cost effective means for mounting the moisture sensors on the windshield of a vehicle is provided. In the present invention, the coupler will generally be mounted on the inner surface of the windshields by the glass manufacturer prior to transporting the windshields to the vehicle manufacturing plant. The vehicle manufacturer conveniently mounts the sensor housing, which includes the circuit board, onto the coupler as the vehicle is being assembled. Because the coupler is small, thin, and relatively inexpensive, the coupler can be mounted on all of the windshields being transported from the glass manufacturer to a specific assembly line at an automotive plant without changing the conventional packaging materials used by the glass manufacturer. As the windshields are installed in a vehicle, the mounting of the sensor can be completed by conveniently attaching the sensor housing to the coupler.

The cost of manufacturing the sensor is reduced by mounting all of the optoelectronic components and signal processing circuitry on a single, planar circuit board. The surface mounted technology and chip-on-board technology combined with automated assembly techniques for production of the circuit board provide an improved efficiency and cost reductions in the manufacture of the sensors. The configuration of the present invention eliminates the use of multiple circuit board and lead formation on the optical devices.

A substantial portion of the light rays emanating from each emitter are coupled into each of the two detectors, providing a high optical efficiency. Additionally, a pair of emitters and a pair of detectors are used to form four optical paths of equal length to provide a balanced optical system having four sensing areas. The numbers of optoelectronic components is reduced which decreases the cost of the sensor without reducing the effectiveness and efficiency of the moisture sensor.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
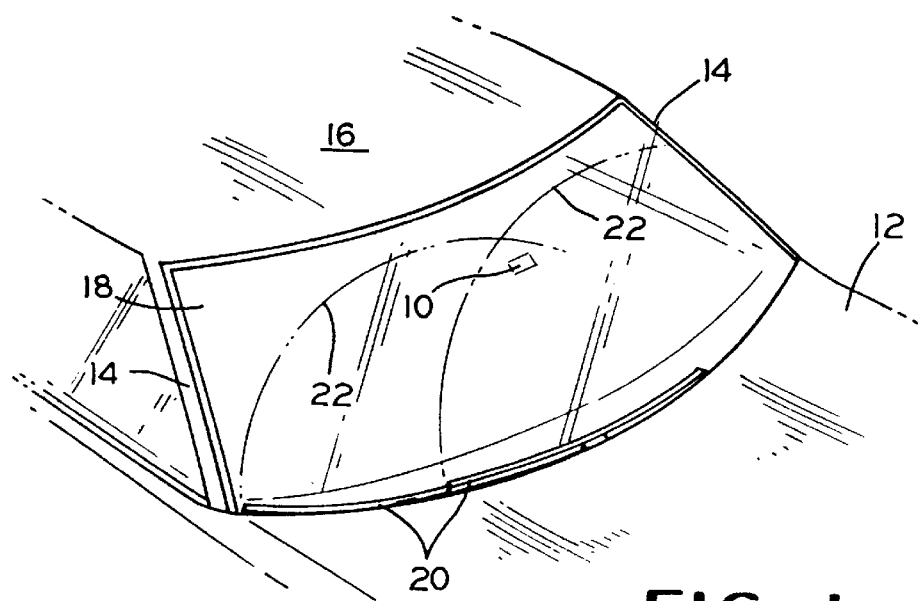
FIG. 1 is a fragmentary perspective view showing an optical moisture sensor mounted upon the windshield of an automobile.

Referring now to FIG. 1, there is shown generally a moisture sensor 10 of the present invention and a portion of an automobile, including a hood 12, side posts 14 and a roof 16 defining an opening within which a windshield 18 is mounted. Windshield wiper blades 20, shown in their at-rest position along the lower edges of the windshield, are operable in a conventional manner to swing in arcs 22 and sweep accumulated moisture from the surface of the windshield 18. The moisture sensor 10 is secured to the windshield within the area swept by windshield wiper blades 20.

Figure 2:
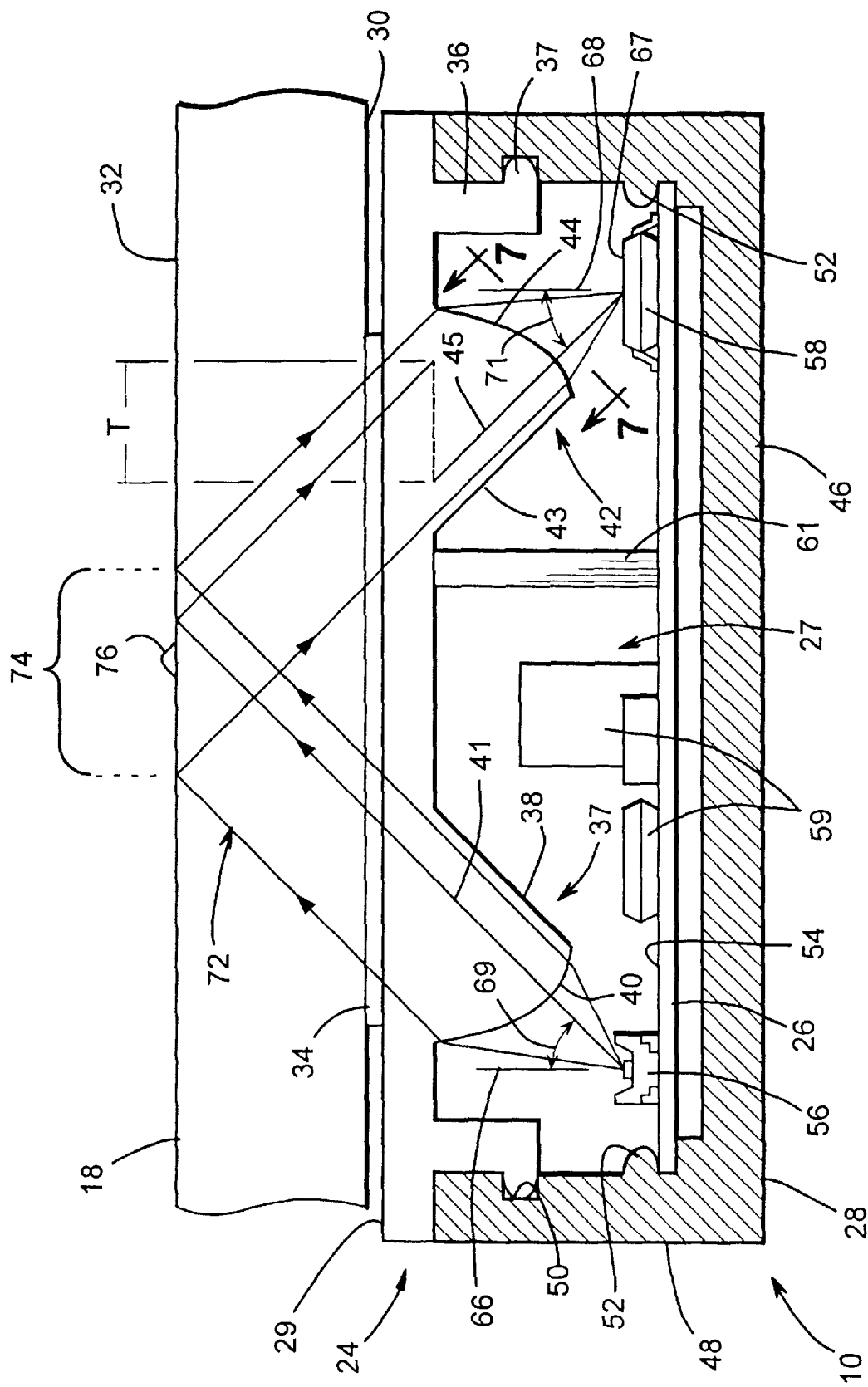
FIG. 2 is an enlarged perspective view showing the mounting of the moisture sensor of the present invention on the inner surface of the windshield.

As shown in FIG. 2, the moisture sensor 10 includes a coupler 24, a circuit board 26 for mounting electronic components 27, and a sensor housing 28 attachable to the coupler 24 for enclosing the circuit board 26.

The coupler 24 includes a mounting surface 29 which is secured to the inner surface 30 of windshield 18 for the optical detection of moisture on the outer surface 32 of the windshield. The moisture sensor 10 is typically mounted adjacent to the rear view mirror (not shown) on the inner surface 30 so as to minimize any view obstruction for the passengers in the automobile, although the sensor may be mounted elsewhere on the windshield. The windshield 18 is generally relatively flat in the area where the sensor 10 is to be mounted, so that the mounting surface 29 of the coupler 24 may be planar. However, it is contemplated that the mounting surface 29 of the coupler 24 may be correspondingly contoured to match a curved windshield surface where appropriate. The sensor 10 may also be mounted on other windows including the rear window.

A double-sided adhesive interlayer 34 is used to secure the coupler mounting surface 29 to the windshield 18 or other window. The interlayer 34 is made from silicone or other similar flexible, transparent plastic material. The coupler 24 may be secured to the windshield 18 by the glass manufacturer prior to transporting the windshield 18 to the automotive assembly line. A rectangular sleeve 36 extends from the coupler 24 opposite the mounting surface 29 and retaining tabs 37 extend outwardly from the ends of the sleeve for securing the coupler to the housing 28 as described below.

The coupler 24 also has a collimator 37 including a collimating body 38 extending from the coupler and a collimating lens 40 disposed adjacent to the collimating body. The collimating lens 40 has an optical axis 41 which extends through the collimating body 38 at a forty-five degree angle with respect to the inner surface of the windshield 30. The coupler 24 further includes a focuser 42 having a focusing body 43 extending from the coupler and a focusing lens 44 disposed adjacent to the focusing body. The focusing lens 44 has an optical axis 45 which extends through the focusing body 43 at a forty-five degree angle with respect to the inner surface of the windshield 30. The coupler 24, collimating body 38, collimating lens 40, focusing body 43 and focusing lens 44 are preferably formed integrally from a single piece of material. The collimating lens 40 is formed by shaping the surface of the collimating body 38, and the focusing lens 44 is formed by shaping the surface of the focusing body 43, in a manner described below. Alternatively, a separate collimating lens 40 may be disposed adjacent to the collimating body 38 and a separate focusing lens 44 may be disposed adjacent the focusing body 43.

The coupler is formed from a refractive material such as polycarbonate, or polyester resin, although any suitable material may be used which can withstand a wide range of temperatures to which an automobile may be subjected. The coupler 24 optically couples light rays into and out of the windshield 18 so that the light rays are not deflected as they pass from the collimating body 38 to the windshield and from the windshield to the focusing body 43. In addition the coupler 24 provides a secure base for mounting the collimating lens 40, focusing lens 44, and housing 28 to the windshield 18.

The thickness of the coupler 24 is an important consideration from a packing standpoint when transporting the windshield from the glass manufacturer to the automotive assembly line. Special racks and packaging material have been designed to pack the individual windshields as close as possible for shipping efficiency while protecting the windshields during transport to prevent scratching or other damage to the windshields. The automotive windshields typically include a mounting button (not shown) on the windshield for mounting the rear view mirror such that the shipping racks can accommodate such mounting button. The coupler 24 of the present invention is less than 5 mm thick, which is thinner than the typical mirror mounting button. Consequently, the thin coupler 24 permits the glass manufacturer to mount the coupler 24 on the windshield production line without having to change the packaging and material handling processes used to deliver the windshields to the automobile assembly line. The ability to mount the coupler at the windshield production operations without changing the packaging and material handling features is an important consideration in gaining increased usage of the moisture sensor and wiper control system by the automotive companies.

Figure 3:
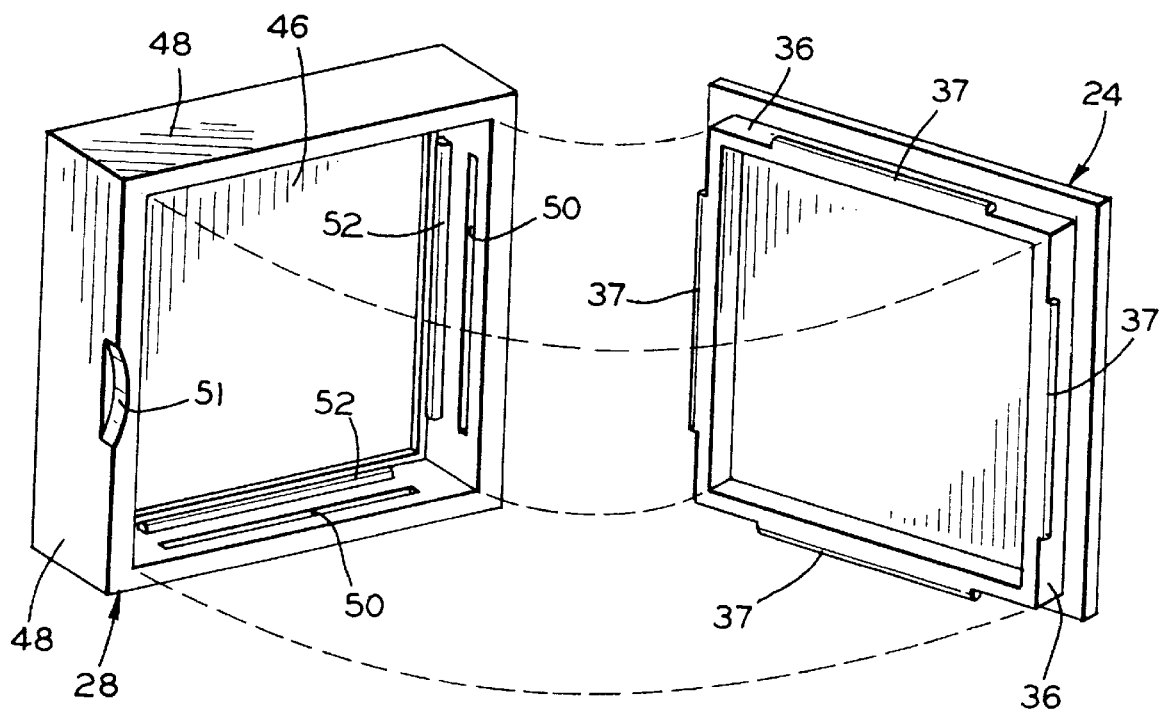
FIG. 3 is an enlarged perspective view showing the mounting relationship between the housing and the coupler of the present invention.

Referring now to FIGS. 2 and 3, the sensor housing 28 is made from a hard plastic or other rigid material and is opaque to block out unwanted light. For clarity, FIG. 3 shows the coupler 24 without showing the collimator or focuser. The housing 28 includes a base 46 and four side walls 48 extending from the base, preferably forming a box-shaped enclosure. The housing 28 is sized to fit over the sleeve 36 of the coupler 24 after the coupler has been secured to the windshield 18. Grooves 50 are formed on the interior of the housing walls 48 for receiving the coupler tabs 37 and detachably retaining the housing 28 to the coupler 24. The side walls 48 of the housing 28, as well as the sleeve 36 of the coupler 24, are each made slightly deformable to facilitate snapping the housing into place over the coupler so that the coupler tabs 37 enter the grooves 50. Optionally, notches may be cut in the sleeve 36 of the coupler 24 to increase the deformation.

Once the housing 28 is snapped in place over the coupler sleeve 36, any lateral forces applied to the coupler 24 are transferred by housing walls 48 to sleeve 36. The housing walls 48 and coupler sleeve 36 have a large surface area, and will have no tendency to concentrate forces which leads to breakage. Further, the non-circular shape of coupler sleeve 36 absorbs torsional forces applied to housing 28. The present moisture sensor will thus tend to remain firmly affixed to the windshield in the event of a collision, or if it is handled clumsily by a curious passenger. A notch 51 in a side wall 48 of the housing 28 facilitates its removal with a coin or screwdriver. Preferably the coupler 24 is autoclaved onto the windshield with the aid of a very high adhesion silicone, although any suitable material may be used. The shallow depth of the coupler attachment method permits such an installation to be performed at the windshield manufacturer, without impacting the pack density of the windshield as described above. Vehicle manufacturers dislike any process dealing with adhesives or other chemicals, and prefer to have the moisture sensor coupler come to them affixed to the windshield.

In addition to making the moisture sensor impact resistant, the perimeter secured design is simple to install. In contrast to moisture sensor attachment methods featuring separate clips or other attachment features, the present moisture sensor housing may be snapped onto the coupler in a one handed operation. This reduces the time it takes the vehicle manufacturer to install the moisture sensor, reducing the cost of the system.

A single, planar circuit board 26 is held in the housing by tabs 52 which extend inwardly from the inner surface of the housing walls. The circuit board 26 includes a device surface 54 on which the electronic components 27 are mounted. The circuit board 26 is mounted in the housing 28 so that the device surface 54 is approximately parallel to the inner surface 30 of the windshield 18 when the housing 28 is secured to the coupler 24 and the coupler is secured to the windshield. The electronic components 27 are mounted on the device surface 54 of the circuit board 26 so that the top surfaces of the electronic components are approximately parallel to the device surface 54. Conventional surface mounting techniques may be used to mount the components on the circuit board 26.

The electronic components 27 include an emitter 56, a detector 58, and signal processing circuitry 59. Although a single emitter 56 and detector 58 are shown, multiple emitters and detectors may be used as described below. The emitter 56 is preferably an infrared light-emitting diode although any suitable emitter may be used, and the detector 58 is preferably a photodiode, although any suitable detector may be used. The emitter 56 and detector 58 are surface mounted devices, such as Siemens part numbers SFH-421 and BPW-34FAS, respectively. The emitter 56 and detector 58 may also be implemented using silicon die bonded directly to the circuit board 26 in a chip-on-board approach.

The signal processing circuitry includes conventional components 59 mounted on the circuit board 26. In addition, light barricades 61 may be mounted on the circuit board to exclude ambient light from the detector 58 and to prevent improper optical communication or crosstalk between the emitter 56 and detector 58 in the housing 28. The emitter 56 and detector 58 are electrically connected to the signal processing. Additional details concerning the operation of the signal processing circuitry and the interface with the controller and the wiper control system may be obtained from U.S. Pat. Nos. 4,620,141; 5,059,877; 5,239,244; and 5,568,027. To the extent any such details may be necessary to complete the descriptions and accounts necessary for purposes of the present application, they are deemed to be incorporated by reference herein.

Figure 4:
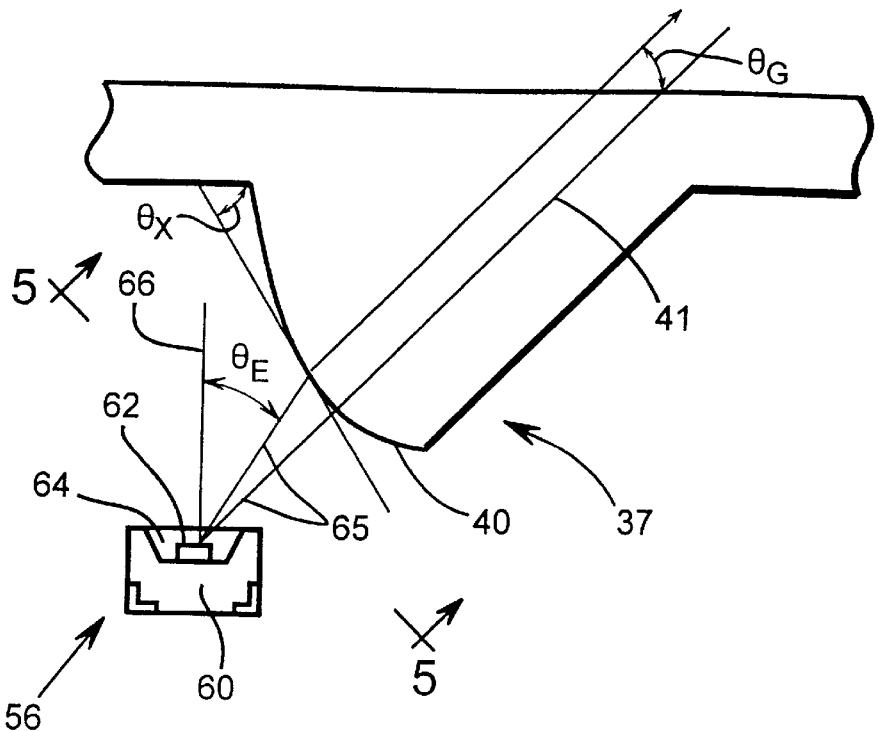
FIG. 4 is a transverse section view showing the collimator mounted adjacent to the emitter in the present invention.

As shown in FIG. 4, the emitter 56 is typically composed of a plastic housing or case 60, an infrared emitting die 62 mounted within a depression in the case, and a clear epoxy filled region 64. The emitter 56 radiates rays of light 65, typically of a specific wavelength such as infrared energy at 880 nM, although other wavelengths may be used. The light rays 65 are emitted as a divergent fan of rays which is symmetric about an emission axis 66 extending from the emitter primarily in a direction perpendicular to the device surface 54 of the circuit board 26. The light rays 65 emanate from the emitter 56 over a splay of angles with each ray traveling at an angle $\theta_E$ with respect to the emission axis 66. The intensity of each of the rays 65 diverging from the emitter 56 is approximately the cosine of $\theta_E$. Thus, the rays 65 from the emitter 56 are strongest along emission axis 66. In the near field in which the invention operates, the rays at an emitter angle $\theta_E$ of greater than about fifty degrees are shadowed by the emitter case 60, and thus are less intense.

As shown in FIG. 2, the detector 58 includes a detection surface 67 extending approximately parallel to the device surface 54. A detection axis 68 of highest detection sensitivity extends from the detection surface 67 in a direction that is primarily perpendicular to the detection surface 67 and the device surface 54 of the circuit board 26. The detector 58 also has an angle of acceptance (not shown) extending symmetrically about the detection axis 68 such that light beams striking the detector within the angle of acceptance will cause the detector 58 to generate a control signal. The specific emitter 56 and detector 58 to be used are chosen so that the detector is sensitive to the wavelength of light emitted by the emitter.

When the housing 28 is secured to the coupler 24 as shown in FIG. 2, the collimating body 38 and collimating lens 40 extend towards the emitter 56 and the focusing body 43 and focusing lens 44 extend towards the detector. A portion of the light rays 65 emanating from the emitter 56 strike the collimating lens 40 and are collimated into a beam 72 traveling through the collimating body 38 along the collimating lens optical axis 41. The light rays which strike the collimating lens 40 preferably range from approximately 10 to approximately fifty degrees with respect to the emission axis 66, although the lens may be shaped to accept light rays from smaller or larger angles. The collimating lens 40 is disposed relative to the emitter 56 such that the optical axis 41 forms an oblique angle 69 with respect to the emission axis 66. The oblique angle 69 is preferably between 39 and 51 degrees although it may be smaller or larger. The surface of the collimating lens 40 must be shaped, as described below, to form a collimated beam of sufficient intensity that the detector 58 can produce a useable signal.

Similarly, the focusing lens 44 is disposed relative to the detector 58 such that the optical axis 45 of the focusing lens 44 forms an oblique angle 71 with respect to the detection axis 68. The oblique angle 71 is preferably between 39 and 51 degrees. The surface of the focusing lens 44 is shaped, as described below, to focus the collimated beam 72 onto the detection surface of the detector. The collimated beam 72 is focused into a fan of convergent rays having sufficient intensity at the detection surface 67 that the detector can produce a useable signal. The fan of light rays converging onto the detection surface preferably range from approximately 10 to approximately fifty degrees with respect to the detection axis, although the fan of rays may form smaller or larger angles with respect to the detection axis.

Light travels from the emitter 56 to the detector 58 along a optical path 73. The light rays from the emitter which are collimated into the collimated beam 72 travel along the optical path into the windshield 18 at a forty-five degree angle with respect to the inner surface 30. The collimated light beam 72 strikes the outer surface 32 at a sensing region 74 and is reflected along the optical path 73 back through the windshield and into the focusing body 43 at a forty-five degree angle with respect to the inner surface 30. The optical axis 45 of the focusing lens 44 is translated from the optical axis 41 of the collimating lens 40 at the surface of the coupler 24 by a distance T. No single light ray travels laterally along this translation; rather it is an artifice indicating that the optical center of the system shifts at the surface of the coupler 24. Distance T is selected so that the focusing lens 44 gathers the full width of beam 72. The collimating surface 40 is a truncated surface of rotation, symmetric about optical axis 41. Translation T of the optical axis 41 to the optical axis 45 comes about because of the nature of the asymetrics of the collimating and focusing apertures. The outside surface of the glass acts as a folding mirror. Because of the effects of this folding mirror, rays close to the emission axis strike the detector at an angle far from the detection axis. Thus, a beam passing through the optical center of the collimator would not pass through the optical center of the focuser lens, which is shifted away from the detection axis.

Figures 5, 6:
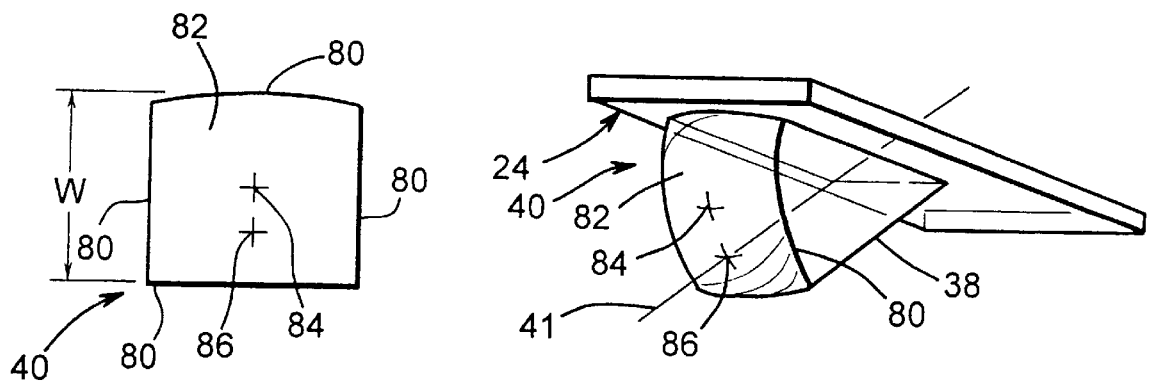
FIG. 5 is a side view taken along line 5—5 showing the collimating lens aperture.
FIG. 6 is a perspective view showing the collimator extending from the coupler in the present invention.

Referring now to FIGS. 5 and 6, the collimating lens 40 has a light receiving aperture 82 defined by the perimeter 80. The perimeter 80 may be the physical edges of the collimating lens 40, or the perimeter 80 may define the area of the lens surface which receives light emitted directly from the emitter 56 and which collimates such light as described above. Light rays that strike the lens surface outside of the aperture 82 are not collimated and are not effectively transmitted to the detector 58. The light receiving aperture 82 has a width W, as shown, measured in the direction of reference line 5—5. The light receiving aperture 82 has a physical center 84 positioned in the center of the perimeter 80.

The optical center of a lens is defined as the point at which an optical axis intersects the lens surface. Also, by definition, a ray of light traveling along the optical axis which enters the lens aperture through the optical center goes straight, whereas all other rays entering the lens aperture are deflected by the lens along a path parallel to the optical axis. The collimating lens 40 has an off-center optical center 86 spaced apart from the physical center 84 and therefore an off-center optical axis 41. Preferably, the optical center 86 is displaced from the physical center 84 by about 22% of width W, although any suitable displacement may be used. The surface of the collimating body 38 of the coupler 24 may optionally be covered with an opaque material to exclude rays that do not strike the aperture 82, or such rays may be allowed to pass through the coupler unobstructed. Additionally, the surface of the collimating lens outside the perimeter 80 defining the aperture 82 may optionally be covered with an opaque material to exclude rays that do not strike the aperture 82, or such rays may be allowed to pass through the coupler unobstructed. Only those emitter rays that pass through aperture 82 are useful for sensing rain.

Figure 7:
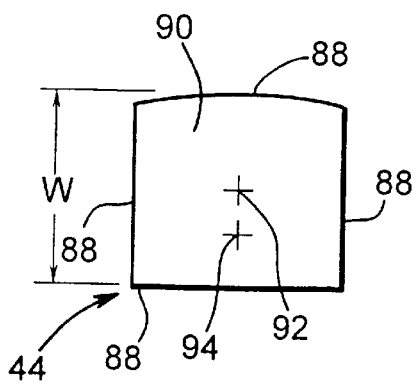
FIG. 7 is a side view taken along line 7—7 showing the collimating lens aperture.

Referring now to FIG. 7, the focusing lens 44 has a light transmitting aperture 90 defined by the perimeter 88. The perimeter 88 may be the physical edges of the focusing lens 44, or the perimeter 88 may define the area of the lens surface which transmits the collimated light beam 72 in a focused beam to the detection surface 67 of the detector 5 8. Light rays that exit the focusing lens outside of the aperture 90 are not focused onto the detector 58. Aperture 90 has a width W, as shown. The focusing lens 44 has a physical center 92 positioned in the center of the perimeter 88. The optical center 94 of the lens 44 is off-center, that is, it is spaced apart from the physical center 92 and, therefore, the focusing lens optical axis 45 is also off-center. Preferably, the optical center 94 is displaced from the physical center 92 by about 22% of width W, although any suitable displacement may be used. The surface of the focusing body 43 of the coupler 24 may optionally be covered with an opaque material to exclude rays that do not strike the aperture 90, or such rays may be allowed to pass through the coupler unobstructed. Additionally, the surface of the focusing lens 44 outside the perimeter 88 defining the aperture 90 may optionally be covered with an opaque material to exclude rays that do not strike the aperture 90, or such rays may be allowed to pass through the coupler unobstructed.

When the moisture sensor is in operation, the controller (not shown) signals the emitter 56 which causes light rays 65 to be emitted symmetrically about the emission axis. The light rays 65 which strike the collimating lens aperture 82 are collimated into a beam 72 traveling along the optical path 73 which is parallel with the collimating lens optical axis 41. The light beam 72 is optically coupled into the interlayer 34 and then into the windshield 18 along the optical path 73. The light beam 72 travels through the windshield 18, continuing at an angle of approximately forty-five degrees and is reflected by the outer surface 32 of the windshield 18 at the sensing region 74. The reflected beam passes back through the windshield 18 along the optical path 73 at a forty-five degree angle with respect to the windshield surface. The collimated light beam 72 travels through the focusing body 43 and the focusing lens 44. The focusing lens focuses the collimated beam 72 onto the surface of the detector 58. If moisture 76 has accumulated on the windshield in the sensing region 74, not all of the collimated light beam 72 will be reflected back to the focusing body 43 and the detector 58 will produce a signal representative of the amount of light which is detected. Although the detector generally has the highest sensitivity when the light beams are perpendicular to the circuit board 26, any light beams 72 within the acceptance angle of the detector 58 will be detected. The signal processing circuitry 59 receives the detector signal and interprets the change in the signal as the presence of moisture and controls the wipers accordingly.

For proper operation, the collimating lens 40 must be positioned with respect to the emitter 56 so that a sufficient amount of the light rays 65 which strike the lens aperture 82 will be collimated. Referring again to FIG. 4, the angle of a line intersecting the surface of the collimating lens 40 with respect to the windshield is shown at $\theta_x$. Values of $\theta_x$ vary over the surface of the collimating lens. As mentioned above, it is preferable that the rays of the collimated light beam 72 travel within the windshield 18 at an angle $\theta_G$ of forty-five degrees with respect to the windshield surface 30. In order for the collimating lens to refract the emitter rays to the required forty-five degree angle, it may be shown by manipulating Snell's law that:

$$\theta_x = \arctan[(\sin(\theta_E) - n \cdot \sin(\theta_G))/(\cos(\theta_E) - n \cdot \cos(\theta_G))]$$

Where n is the refractive index of the coupler 24. The coupler 24 is preferably molded from polycarbonate, having a refractive index of n=1.57 at 880 nM. Alternatively, the coupler may be fabricated from glass, acrylic, or some other clear material. From this equation, it may be shown for example that for an emitter angle $\theta_E$ of 10 degrees, a collimating lens surface angle of 76 degrees is required. At such a steep angle, about half of the intensity of the beam from the emitter is reflected off of the collimating lens surface, and thus does not enter the windshield 18. The reflection increases dramatically at even smaller emitter angles. Therefore, this relationship between the emitter angle and the collimating lens surface angle establishes a lower limit on the distance between the collimator lens 40 and the emission axis 66. Similarly, the same lower limit is placed on the distance between the focusing lens 44 and the detection axis 68. Light rays passing through the focusing lens 44 closer than about 10 degrees to the detection axis 68 will internally reflect off the inside surface of the focusing lens 44 and reduce the intensity of the focused beam that reaches the detection surface 67.

Other effects establish an upper limit on the distance between the emission axis 66 and the collimator lens 40. As $\theta_E$ increases, obliquity reduces the strength of the emitter beam which varies according to $\cos \theta_E$ as described above. Also, at values of $\theta_E$ of about fifty degrees, the emitted light rays are shadowed by emitter case 60. Thus, the range of angles which may be usefully coupled into the windshield 18 is confined to emitter angles between about 10 and about fifty degrees. Again, at smaller angles, too large a fraction of the beam is reflected off of the collimator lens surface. At larger angles, obliquity reduces the strength of the emitted light, and the light is shadowed by the case of the emitter. Within this range of emitter angles, effects of reflection and obliquity roughly cancel. Thus, the emitted light rays are reasonably uniform within the prescribed range of emitter angles. This restriction of the emitter beam carries a further advantage in that it allows the design to fit within the 5 mm height requirement of the coupler. A wider range of emitter rays would require a taller coupler. Similarly, light rays traveling in excess of about fifty degrees from the detection axis 68 will be received poorly by the detector 58 due to high obliquity. As with the collimator 37, restricting the angles of the rays received from the focusing lens 44 by the detector 58 permits a shallow coupler 24 design.

The surface of the collimating lens 40 is shaped to allow the collimating lens to collimate a large portion of the light rays traveling from the emitter when the emission axis 66 forms an oblique angle with respect to the optical axis 41. Preferably, the surface of the collimating lens is a continuous, convex refractive surface, although the surface may be segmented as described below. The appropriate shape of the lens surface can be determined using an optical design software system, such as the Zemax system by Focus Software in Tucson, Ariz. The resulting surface shape is best represented by a polynomial asphere. The surface is given by a sag function, which generates the distance z between the surface and the radius from the optical axis. That surface may be, for purposes of illustration:

$$z = (cr^2)/(1+\sqrt{1-(1+k)c^2 r^2}) + a_1 r^2 + a_2 r^4 + a_3 r^6 a_4 r^8 +$$

Where:

| Where: | |
|---|---|
| Coefficient | Value |
| r | infinity |
| c | 0 |
| $a_1$ | 0.22631484 |
| $a_2$ | −0.018779505 |
| $a_3$ | 0.0010712278 |
| $a_4$ | 0 |

This method of describing an aspheric lens is familiar to those skilled in the art of optical system design. Alternatively, a spherical lens of radius 3.163 mm may be substituted, however, aberration is induced which may reduce the intensity of the light transmitted by the lens. The values given will allow slight divergency of the collimated beam, easing the tolerance requirements of the emitter placement.

Figure 8:
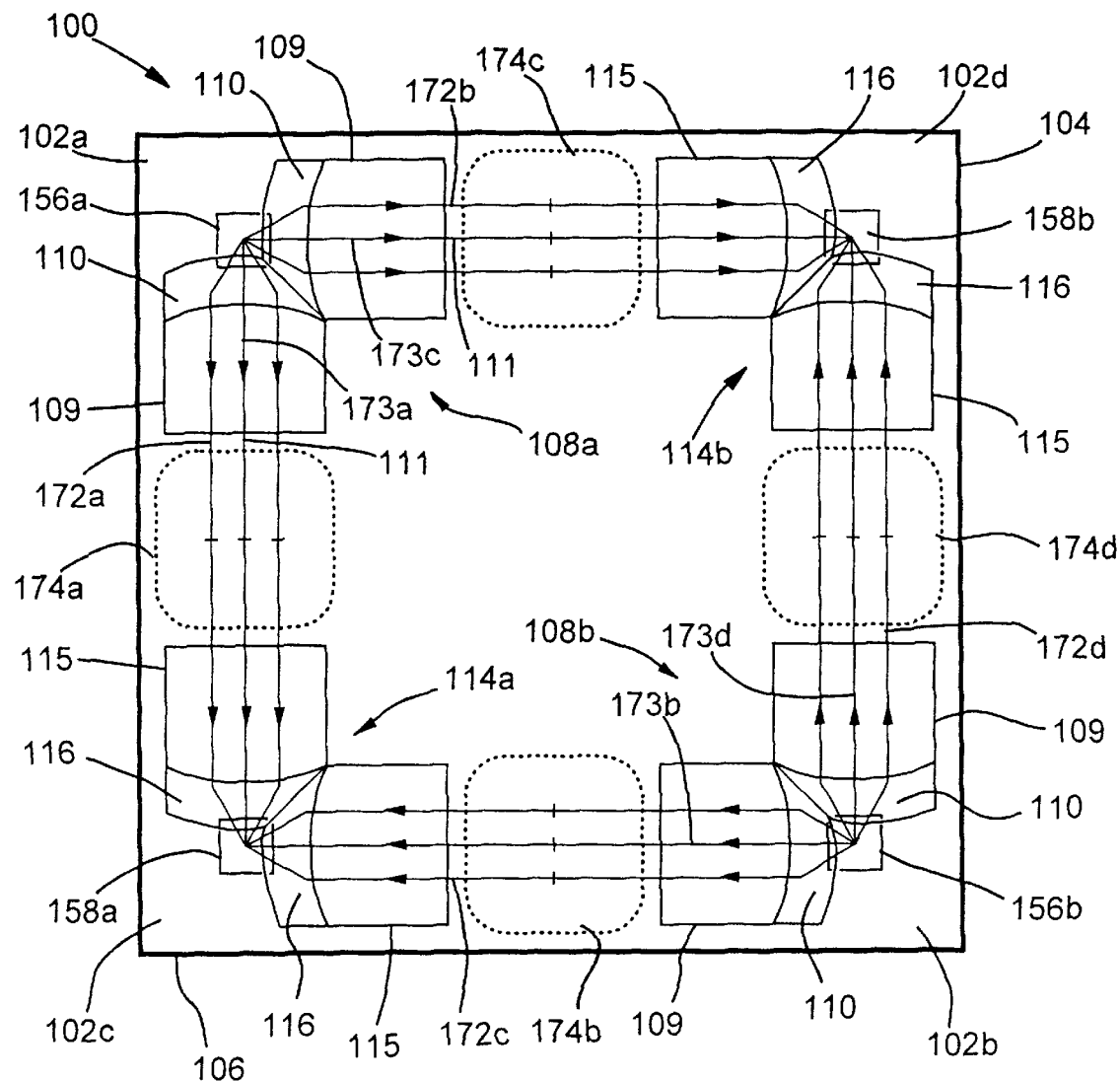
FIG. 8 is a plan view of an alternative embodiment of the present invention illustrating the four optical paths.

Although only one optical path is required to make a functioning moisture sensor, a single optical path may provide a sensing area of inadequate surface area for smooth operation of the wipers. Referring now to FIG. 8, an alternative embodiment of the present invention is provided with a different arrangement of optical components providing multiple optical paths. The sensor 100 of the alternative embodiment includes a first and second emitter 156a and 156b, and a first and second detector 158a and 158b, mounted to a circuit board device surface (not shown) in a manner similar to that described above. The first emitter 156a is located on the circuit board (not shown) at a first corner 102a of a square 104 and the second emitter 156b is located on the circuit board at a second corner 102b opposite the first corner 102a. The first and second emitters 156a and 156b include emission axes (not shown) similar to the emission axis 69 of the emitter 56 shown in FIG. 4. The first detector 158a is located on the circuit board at a third corner 102c of the square 104 and the second detector 158b is located on the circuit board at a fourth corner 102d opposite the third corner 102c. The first and second detectors 158a and 158b include detection axes (not shown) similar to the detection axis 68 of the detector 56 shown in FIG. 4. The circuit board is mounted in a housing 28 shown in FIG. 3 in a manner similar to the circuit board 26 described above.

The sensor 100 includes a coupler 106 having a mounting surface (not shown) which is mounted to the windshield in a manner similar to the coupler 24 described above. The housing 28 is attached to the coupler 106 in a similar manner as coupler 24 described above. The coupler 106 includes a first collimator 108a located adjacent the first emitter 156a at the first corner 102a when the housing 28 is attached to the coupler 106. The coupler 106 also includes a second collimator 108b located adjacent the second emitter 156b at the second corner 102b when the housing 28 is attached to the coupler 106. Each collimator 108a and 108b includes two collimating bodies 109 and two collimating lenses 110. The two collimating lenses 110 abut each other so that their optical axes 111 form an approximate ninety degree angle when viewed as shown in FIG. 8. The collimating lenses 110 are preferably formed integrally with the collimating bodies 109, although separate lenses may be disposed adjacent each collimating body as described above.

Each of the collimating lenses 110 are similar to the collimating lens 40 described above and to avoid duplication shall not be described in such detail. Each collimating lens 110 has a physical center, an optical center, and an optical axis similar to the physical center 84, optical center 86, and optical axis 41 of the collimating lens 40 as shown in FIGS. 4, 5 and 6, collimating lenses 110 of the first collimator 108a are disposed adjacent the first emitter 156a such that each of the optical axes forms an oblique angle with respect to the emitter axis described above. The collimating lenses 110 of the second collimator 108b are disposed adjacent the second emitter 156b such that each of the optical axes forms an oblique angle with respect to the emitter axis described above. The surface of the collimating lenses 110 are formed similarly to the collimating lens 40 described above such that the optical center is offset from the physical center for the reasons described above.

The coupler 106 also includes a first focuser 114a located adjacent the first detector 158a at the third corner 102c when the housing 28 is attached to the coupler 106. The coupler 106 further includes a second focuser 114b located adjacent the second detector 158b at the fourth corner 102d when the housing 28 is attached to the coupler 106. Each focuser 114a and 114b includes two focusing bodies 115 and two focusing lenses 116. The two focusing lenses 116 abut each other so that their optical axes 117 form an approximate ninety degree angle when viewed as shown in FIG. 8. The focusing lenses 116 are preferably formed integrally with the focusing bodies 115, although separate lenses may be disposed adjacent each focusing body as described above. A corner of each collimating lens 110 and focusing lens 116 is removed to allow the juxtaposition but the performance of the lenses is not adversely affected.

Each of the focusing lenses 116 are similar to the focusing lens 44 described above and to avoid duplication shall not be described in such detail. Each focusing lens 116 has a physical center, an optical center, and an optical axis similar to the physical center 92, optical center 94, and optical axis 45 of the focusing lens 44 as shown in FIGS. 2 and 7. The focusing lenses 116 of the first focuser 114a are disposed adjacent the first detector 158a such that each of the optical axes forms an oblique angle with respect to the emitter axis described above. The focusing lenses 116 of the second focuser 114b are disposed adjacent the second detector 158b such that each of the optical axes forms an oblique angle with respect to the emitter axis described above. The surface of the focusing lenses 116 are formed similarly to the focusing lens 44 described above such that the optical center is offset from the physical center for the reasons described above.

Four optical paths 173a, 173b, 173c, and 173d are provided. The first optical path 173a extends from the first emitter 156a through a collimator lens 110 and collimator body 109 of the first collimator 108a, into the windshield at a forty-five degree angle with respect to the inner surface to a first sensing area 174a, back through the windshield at a forty-five degree angle with respect to the windshield inner surface, through a focusing body 115 and focusing lens 116 of the first focuser 114a to the first detector 158a. The second optical path 173b extends from the second emitter 156b through a collimator lens 110 and collimator body 109 of the second collimator 108b, into the windshield at a forty-five degree angle with respect to the inner surface to a second sensing area 174b, back through the windshield at a forty-five degree angle with respect to the windshield inner surface, through the focusing body 115 and focusing lens 116 of the first focuser 114a to the first detector 158a.

The third optical path 173c extends from the first emitter 156a through a collimator lens 110 and collimator body 109 of the first collimator 108a, into the windshield at a forty-five degree angle with respect to the inner surface to a second sensing area 174c, back through the windshield at a forty-five degree angle with respect to the windshield inner surface, through the focusing body 115 and focusing lens 116 of the second focuser 114b to the second detector 158b. The fourth optical path 173b extends from the second emitter 156b through the collimator lens 110 and collimator body 109 of the second collimator 108b, into the windshield at a forty-five degree angle with respect to the inner surface to a fourth sensing area 174d, back through the windshield at a forty-five degree angle with respect to the windshield inner surface, through the focusing body 115 and focusing lens 116 of the second focuser 114b to the second detector 158b.

In operation, the emitters 156a and 156b emit diverging light rays into a hemisphere so that each of the adjacent collimator lenses 110 receives an equal amount of light. The two collimating bodies 109 and lenses 110 at the first collimator 108a produce first and second collimated light beams 172a and 172b, similar to the collimated beam 72 described above. The first and second collimated light beams 172a and 172b are splayed at right angles to each other when viewed as shown in FIG. 8, and each light beam travels along the first and third optical path 173a and 173c respectively. The two collimating bodies 109 and lenses 110 at the second collimator 108b produce third and fourth collimated light beams 172c and 172d, similar to the collimated beam 72 described above. The third and fourth collimated light beams 72c and 72d are splayed at right angles to each other, and each light beam travels along the second and fourth optical path 173b and 173d respectively.

The first collimated light beam 172a is reflected by the outside surface of the windshield at the first sensing area 174a, back through the focusing body 115 and focusing lenses 116 to the first detector 158a. If moisture is present in the first sensing area on the outside surface of the windshield, some of the collimated light beam will not be reflected back into the focuser 114 and the first detector 158a will emit a signal corresponding to the change in the light detected. The signal will be processed by signal processing circuitry (not shown) similar to the signal processing circuitry 59 shown in FIG. 2 and the wipers will be controlled accordingly. Similarly, the second, third and fourth collimated light beams will reflect off of the corresponding sensing areas, and the first or second detector will detect any changes in the light received. By using four sensing areas, the moisture sensor 100 can provide improved wiper control and enhanced visibility.

The arrangement of the optical components in the alternate embodiment moisture sensor 100 provides a balanced optical system because the four optical paths 102 are of equal length and equal optical efficiency. This arrangement will compensate for differences in efficiency between emitters 56, which may vary considerably. Both detectors 58 will receive an equal amount of light from a particular emitter, and the sum of the light received from both emitters will be the same for each detector.

Figure 9:
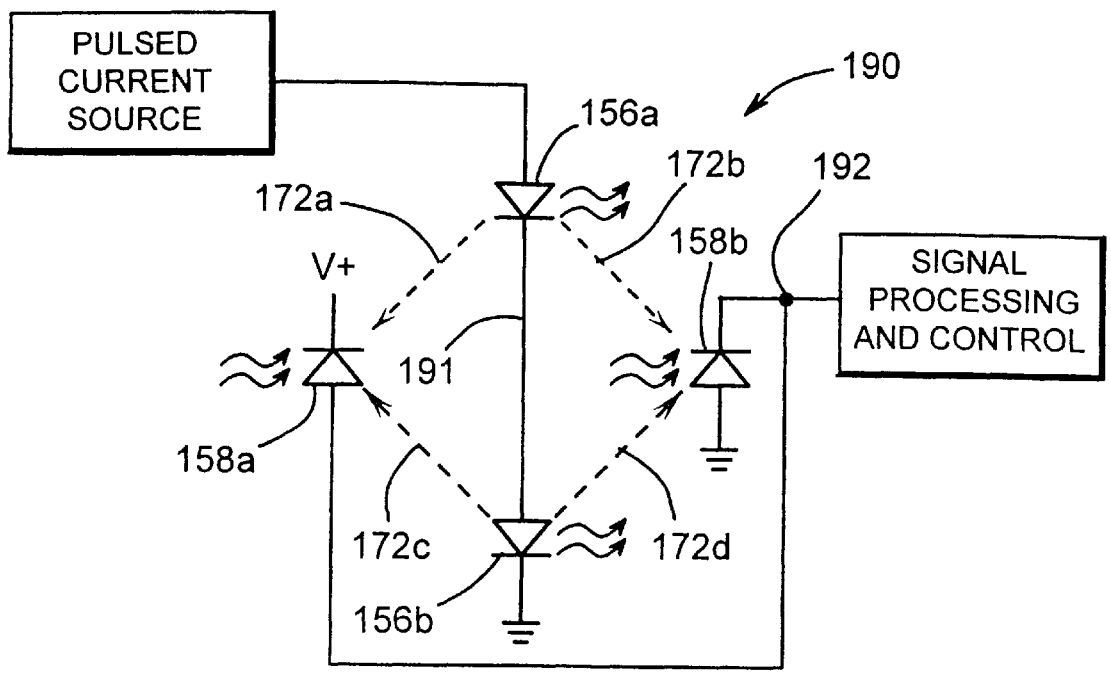
FIG. 9 is a schematic diagram illustrating the optoelectronic components of the alternative embodiment of the present invention.

Referring to FIG. 9, a balanced electrical system 190 is shown for use in conjunction with the above described balanced optical system to provide a balanced moisture sensor system. A pulsed current source drives emitters 156a and 156b, which are preferably connected in series by line 191. A light beam (represented by dashed lines 172a, 172b, 172c, 172d) traveling along an optical path couples each emitter 156a, 156b to each detector 158a, 158b. Each optical path has an equal length and a similar optical efficiency. The detectors 158a, 158b function in current mode, and are connected together into a common current summing node 192. Signal processing and control circuitry connected to node 192 detects the presence of rain. For a perfectly balanced moisture sensor system, no current will flow from node 192 to the signal processing and control circuitry in the absence of rain. A balanced moisture sensor system is desirable because it requires less dynamic range from the signal processing circuitry and it enhances the ability of the system to reject ambient light.

Modem solar-control windshields, such as windshields sold under the trademark "EZ-KOOL" commercially available from Libby Owens Ford, Co., reduce the passage of infrared light through the windshield. Optical moisture sensors used on such windshields must have a high efficiency since the windshield reduces the transmittance of the infrared beam from the emitter to the detector. The moisture sensor 100 described above provides an efficient sensor capable of use with these solar-controlled windshields. Moisture sensors as described above have been tested on "EZ-KOOL" brand solar-control windshields using couplers composed of polyester casting resin which produce 17 microamps per amp of emitter current which is sufficient for typical signal processing circuitry. The moisture sensor provided a combined sensing area of 57 square millimeters using only two emitters and two detectors, and production versions will probably have even greater sensing areas.

Figure 10:
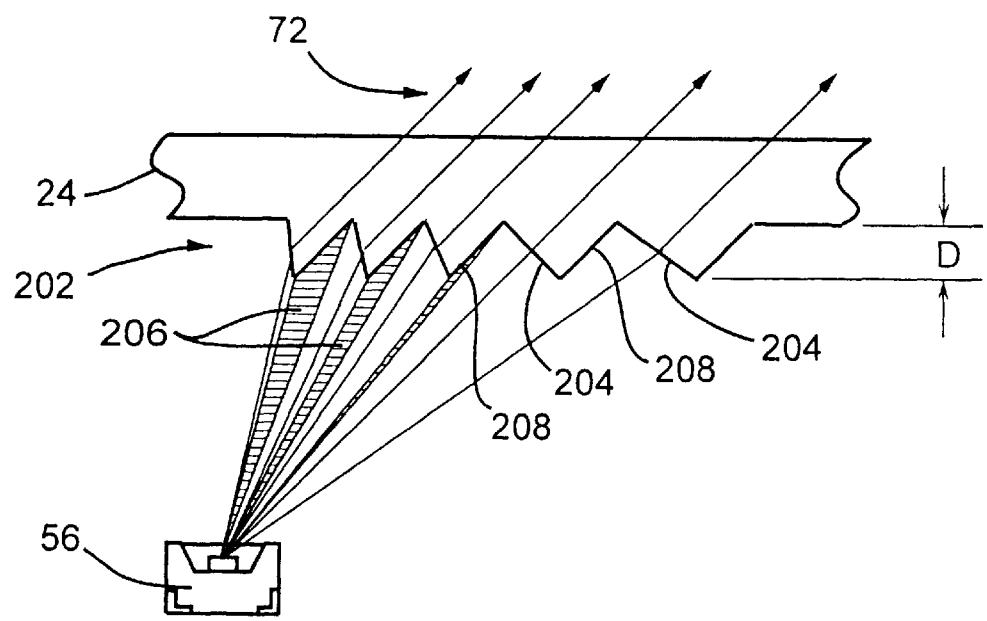
FIG. 10 is a transverse section view of a second alternative embodiment of the present invention illustrating the collimating lens using a segmented lens.

Referring now to FIG. 10, an alternate embodiment of a collimator lens is shown using a segmented lens, or Fresnel lens 202 rather than the continuous, convex lens 40 discussed above. The Fresnel lens 202 may also be used as the focusing lens in place of the continuous, convex focusing lens 44 discussed above. Due to the similarity between the collimating lens and the focusing lens as discussed above, only a Fresnel lens collimator is discussed. A similar Fresnel lens can be used for the focuser which performs similarly to the continuous, convex lens focuser 40 described above.

The Fresnel collimator lens 202 has the advantage that the lens region, and thus the moisture sensor as a whole, may be made still thinner. The resulting thinner coupler 24 comes at the expense of some optical efficiency, and a somewhat more complex mold needed to form the coupler and lenses 202. Such a lens may be constructed by projecting the surface of the collimator lens of FIGS. 4 and 6 onto the inside surface of the coupler 24, permitted to extend to a depth D in a modulo operation. This results in collimator lens 202 comprised of a number of refracting segments 204. Note that, in contrast to the common construction of a Fresnel lens, the plane of projection of the light rays is not orthogonal to the optical axis, but rather angled to provide reflection at the outer surface of the glass as described above. Alternatively, optical design programs such as the aforementioned Zemax may be used to generate the required surface directly, using suitable tilt commands to achieve the desired plane of projection. As a further method of generating the surface, the formula derived from Snell's law above may be employed to generate the required angles.

The disadvantage of the segmented approach is that it creates occlusion regions, such as shown at 206. Occlusion regions 206 occur when light rays strike a non-useful return segment 208. Such segments are needed to keep the geometry of the lens within depth D. The occlusion regions 206, however, are not capable of directing light in the desired direction and degrade the optical efficiency of the system. The multipath configuration of the invention, as shown in FIG. 8, is not modified. Similarly, the attachment method is unchanged. The Fresnel approach may be fabricated with many segments, as shown, or with as few as two. Also, while it is preferred that the projection be onto the plane of the inside wall of the coupler, the plane of projection may be tilted somewhat toward the optical devices. Such an implementation would require fewer occlusion regions.

In addition to the front windshield of a motor vehicle, the moisture sensor of the present invention can also be used on other glass surfaces for the detection of moisture.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A moisture sensor for mounting on a first surface of a sheet of glass to detect moisture in a sensing area on a second surface of the sheet of glass, said moisture sensor comprising:

a) a coupler for mounting on the first surface of the sheet of glass for optically coupling light rays into and out of the glass;

b) a housing secured to said coupler;

c) a planar circuit board secured in said housing and having a device surface which is disposed generally parallel to the first surface of the sheet of glass;

d) an emitter mounted on said device surface for emitting light rays about an emission axis extending from said emitter approximately perpendicular to said device surface;

e) a collimator optically coupled to said coupler for collimating light rays from said emitter into a collimated light beam, said collimator having a light receiving aperture with a physical center and an optical center such that an optical axis extends through said optical center and said optical center is spaced apart from said physical center, said collimator being disposed such that the optical axis forms a first oblique angle with respect to the emission axis;

f) a detector having a detection surface and a detection axis extending from the detection surface for detecting light striking the detection surface about the detection axis and for generating signals in response to the detected light, said detector mounted on the device surface of said planar circuit board such that the detection axis is approximately perpendicular to the device surface; and g) a focuser optically coupled to said coupler for focusing the collimated light beam into a convergent fan of rays onto said detection surface, said focuser having a light transmitting aperture with a physical center and an optical center such that an optical axis extends through said optical center and said optical center is spaced apart from said physical center, said focuser being disposed such that said optical axis forms a second oblique angle with respect to said detection axis.

2. The moisture sensor of claim 1 wherein said collimator includes a collimating lens, and said focuser includes a focusing lens.

3. The moisture sensor of claim 2 wherein said coupler, said collimator, said collimating lens, said focuser and said focusing lens are formed integrally from a single piece of material.

4. The moisture sensor of claim 1 further including a signal processing circuit mounted on said circuit board and connected to said emitter and said detector for controlling the light emitted by said emitter and for processing the signals from said detector.

5. The moisture sensor of claim 1 wherein said first oblique angle is between thirty-nine and fifty-one degrees and said second oblique angle is between thirty-nine and fifty-one degrees.

6. The moisture sensor of claim 1 wherein said optical center of said collimator light receiving aperture is displaced at least 20% of the width of said light receiving aperture from said physical center of said light receiving aperture.

7. The moisture sensor of claim 1 wherein said optical center of said focuser light transmitting aperture is displaced at least 20% of the width of said light transmitting aperture from said physical center of said light transmitting aperture.

8. The moisture sensor of claim 1 wherein said collimator is disposed to collimate light rays emitted from said emitter, wherein said light rays range from approximately ten to approximately fifty degrees with respect to said emission axis.

9. The moisture sensor of claim 1 wherein said focuser is disposed to focus a collimated light beam into a convergent fan of rays onto said detection surface, wherein said fan of light rays range from approximately ten to approximately fifty degrees with respect to said detection axis.

10. The moisture sensor of claim 2 wherein said collimating lens and said focusing lens are continuous convex lenses.

11. The moisture sensor of claim 1 wherein said collimator includes a segmented collimating lens and said focuser includes a segmented focusing lens.

12. The moisture sensor of claim 2 further wherein said collimator includes a second collimating lens and said focuser includes a second focusing lens, and said moisture sensor further including a second emitter and a second detector mounted on said device surface, a second collimator optically coupled to said coupler and including third and fourth collimating lenses, and a second focuser optically coupled to said coupler and including third and fourth focusing lenses, wherein light rays from both emitters are collimated into light beams and said light beams are focused onto both detectors.

13. A moisture sensor for mounting on a first surface of a sheet of glass to detect moisture in a plurality of sensing areas on a second surface of the sheet of glass, said moisture sensor comprising:

a) a housing;

b) first and second emitters disposed in said housing for emitting light rays;

c) a first detector disposed in said housing for detecting light rays traveling along a first optical path extending from said first emitter to the second surface of said glass at one of the sensing areas and back to said first detector and for detecting light rays traveling along a second optical path extending from said second emitter to the second surface of said glass at one of the sensing areas and back to said first detector, wherein the length of said second optical path is approximately equal to the length of said first optical path; and d) a second detector disposed in said housing for detecting light rays traveling along a third optical path extending from said first emitter to the second surface of said glass at one of the sensing areas and back to said second detector and for detecting light rays traveling along a fourth optical path extending from said second emitter to the second surface of said glass at one of the sensing areas and back to said second detector, wherein the lengths of said third and fourth optical paths are approximately equal to the length of said first optical path.

14. The moisture sensor of claim 13 further including a coupler having collimators for collimating a portion of light rays emitted from said emitters about emission axes extending perpendicularly with respect to the first surface of the sheet of glass into collimated light beams traveling along said optical paths, and focusers for focusing said collimated beams into convergent rays onto said detectors having detection axes extending perpendicularly with respect to the first surface of the sheet of glass.

15. The moisture sensor of claim 14 wherein said collimators include a light receiving aperture with a physical center and an optical center such that an optical axis extends through said optical center and said optical center is spaced apart from said physical center, said collimators being disposed such that said optical axes form first oblique angles with respect to said emission axes, and wherein said focusers include a light transmitting aperture with a physical center and an optical center such that an optical axis extends through said optical center and said optical center is spaced apart from said physical center, said focusers being disposed such that said optical axes form second oblique angles with respect to said detection axes.

16. A moisture sensor for mounting on a first surface of a sheet of glass to detect moisture in a plurality of sensing areas on a second surface of the sheet of glass, said moisture sensor comprising:

a) a first emitter for emitting light rays disposed at a first corner of a square;

b) a second emitter for emitting light rays disposed at a second corner of the square, opposite the first corner;

c) a first collimator disposed adjacent said first emitter for collimating light rays emitted from said first emitter into a first and second collimated light beam;

d) a second collimator disposed adjacent said second emitter for collimating light rays emitted from said second emitter into a third and fourth collimated light beam;

e) a first detector disposed at a third corner of the square for detecting said first collimated light beam traveling along a first optical path between said first emitter and said first detector and said third collimated light beam traveling along a second optical path between said second emitter and said first detector, said second optical path having a length approximately equal to said first optical path, and for generating signals in response to the detected light beams; and f) a second detector disposed at a fourth corner of the square opposite the third corner for detecting said second collimated light beam traveling along a third optical path between said first emitter and said second detector and said fourth collimated light beam traveling along a fourth optical path between said second emitter and said second detector, said third and fourth optical paths each having a length approximately equal to said first optical path, and for generating signals in response to the detected light beams.

17. A moisture sensor for mounting on a first surface of a sheet of glass to detect moisture in a sensing area on a second surface of the sheet of glass, said moisture sensor comprising:

a) a coupler having a mounting surface for mounting on the first surface of the sheet of glass for coupling light rays into and out of the glass;

b) a sleeve disposed about the perimeter of said coupler and extending from said coupler opposite said mounting surface;

b) tabs extending outwardly from said sleeve;

c) a housing for fitting over said sleeve having a base and side walls extending from said base, said side walls having interior surfaces with grooves formed therein, said housing detachably fitting over said sleeve such that said tabs extend into said grooves for securing said housing to said coupler;

d) a planar circuit board secured in said housing and having a device surface for receiving electronic components;

e) an emitter mounted on said device surface for emitting light rays symmetrically about an emission axis; and f) a detector mounted on said device surface having a detection surface for detecting light emitted by said emitter and for generating control signals in response to said detected light.

18. The moisture sensor of claim 17 further including a collimator extending from the surface of said coupler opposite said mounting surface for collimating light rays emitted from said emitter into a collimated light beam, and a focuser extending from the surface of said coupler opposite said mounting surface for focusing the collimated light beam into a convergent fan of light rays onto said detection surface.

19. The moisture sensor of claim 18 wherein said emitter includes an emission axis extending from said emitter approximately perpendicular to said device surface, and said detector includes a detection axis extending from said detection surface approximately perpendicular to said device surface.

20. The moisture sensor of claim 19 wherein said collimator includes a light receiving aperture with a physical center and an optical center such that an optical axis extends through said optical center and said optical center is spaced apart from said physical center, said collimator being disposed such that the optical axis forms a first oblique angle with respect to the emission axis, and said focuser includes a light transmitting aperture with a physical center and an optical center such that an optical axis extends through said optical center and said optical center is spaced apart from said physical center, said focuser and said detector being disposed such that said optical axis forms a second oblique angle with respect to said detection axis.

* * * * *